(12) United States Patent
Yamada (10) Patent No.: US 9,901,754 B2
(45) Date of Patent: Feb. 27, 2018

(54) GRASPING TREATMENT APPARATUS AND GRASPING UNIT

(71) Applicant: OLYMPUS CORPORATION, Tokyo (JP)

(72) Inventor: Masashi Yamada, Sagamihara (JP)

(73) Assignee: OLYMPUS CORPORATION, Tokyo (JP)

(*) Notice: Subject to any disclaimer, the term of this patent is extended or adjusted under 35 U.S.C. 154(b) by 0 days.

(21) Appl. No.: 14/928,197

(22) Filed: Oct. 30, 2015

(65) Prior Publication Data
US 2016/0045770 A1    Feb. 18, 2016

Related U.S. Application Data

(63) Continuation of application No. PCT/JP2014/063812, filed on May 26, 2014.

(30) Foreign Application Priority Data

Aug. 29, 2013  (JP) .................................. 2013-178687

(51) Int. Cl.
*A61B 18/12* (2006.01)
*A61N 7/00* (2006.01)
(Continued)

(52) U.S. Cl.
CPC ........ *A61N 7/00* (2013.01); *A61B 17/320068* (2013.01); *A61B 17/320092* (2013.01);
(Continued)

(58) Field of Classification Search
CPC ...... A61B 17/320068; A61B 1/320092; A61B 18/1445; A61B 2017/2825;
(Continued)

(56) References Cited

U.S. PATENT DOCUMENTS 5,891,142 A * 4/1999 Eggers ............... A61B 18/1442
606/51
2005/0021027 A1* 1/2005 Shields .............. A61B 18/1445
606/51
(Continued)

FOREIGN PATENT DOCUMENTS

CN    101396300 A    4/2009
EP    0640317 A1    3/1995
(Continued)

OTHER PUBLICATIONS

Mar. 10, 2016 International Preliminary Report on Patentability issued in PCT/JP2014/063812.
(Continued)

*Primary Examiner* — Daniel Fowler
(74) *Attorney, Agent, or Firm* — Oliff PLC (57) ABSTRACT

A jaw of a grasping treatment apparatus includes abutment portion spacing a distal treatment section and a jaw electrode portion apart from each other in a state that the abutment portion abuts on the distal treatment section, and a jaw insulation portion disposed in a part spaced apart from the abutment portion in a width direction of the jaw on an electrode facing-surface. a spacing distance from the distal treatment section to an insulation facing-surface is less than a distance from the electrode facing-surface to the distal treatment section in the state that the abutment portion abuts on the distal treatment section.

6 Claims, 8 Drawing Sheets

(51) Int. Cl.
    *A61B 17/32*     (2006.01)
    *A61B 18/14*     (2006.01)
    *A61B 17/29*     (2006.01)
    *A61B 17/28*     (2006.01)
    *A61B 90/00*     (2016.01)

(52) U.S. Cl.
    CPC .. *A61B 18/1445* (2013.01); *A61B 2017/2825* (2013.01); *A61B 2017/2916* (2013.01); *A61B 2017/2926* (2013.01); *A61B 2017/320088* (2013.01); *A61B 2090/034* (2016.02)

(58) Field of Classification Search
    CPC .... A61B 2017/2916; A61B 2017/2926; A61B 2017/320088; A61N 7/00
    See application file for complete search history.

(56) References Cited

U.S. PATENT DOCUMENTS

| | | | |
|---|---|---|---|
| 2008/0132887 A1* | 6/2008 | Masuda | A61B 18/1445 606/37 |
| 2009/0088785 A1 | 4/2009 | Masuda | |
| 2013/0066238 A1 | 3/2013 | Irisawa et al. | |

FOREIGN PATENT DOCUMENTS

| | | |
|---|---|---|
| EP | 1568330 A1 | 8/2005 |
| EP | 2042112 A2 | 4/2009 |
| JP | 2000-102545 A | 4/2000 |
| JP | 2009-082711 A | 4/2009 |
| JP | 2009-240773 A | 10/2009 |
| WO | 2012/108295 A1 | 8/2012 |

OTHER PUBLICATIONS

Aug. 19, 2014 Search Report issued in International Patent Application No. PCT/JP2014/063812.

May 12, 2015 Office Action issued in Japanese Patent Application No. 2015-509661.

Jan. 3, 2017 Office Action issued in Chinese Patent Application No. 201480031351.7.

Mar. 24, 2017 Search Report issued in European Patent Application No. 14841277.8.

\* cited by examiner

GRASPING TREATMENT APPARATUS AND GRASPING UNIT

CROSS-REFERENCE TO RELATED APPLICATIONS

This is a Continuation application of PCT Application No. PCT/JP2014/063812, filed May 26, 2014 and based upon and claiming the benefit of priority from prior Japanese Patent Application No. 2013-178687, filed Aug. 29, 2013, the entire contents of which are incorporated herein by reference.

BACKGROUND OF THE INVENTION

1. Field of the Invention

The present invention relates to a grasping treatment apparatus including a distal treatment section to which an ultrasonic vibration is configured to be transmitted, and a jaw (grasping unit) which is openable and closable relative to the distal treatment section, the grasping treatment apparatus being configured to treat a treatment target that is grasped between the distal treatment section and the jaw.

2. Description of the Related Art

Jpn. Pat. Appln. KOKAI Publication No. 2009-240773 discloses a grasping treatment apparatus including an ultrasonic probe serving as a vibration transmission portion, a distal portion of which is provided with a distal treatment section, and a jaw (grasping unit) which is openable and closable relative to the distal treatment section. In the ultrasonic probe, an ultrasonic vibration is transmitted to the distal treatment section from a proximal direction toward a distal direction. In addition, a high-frequency current is transmitted to the distal treatment section via the ultrasonic probe, and thereby the distal treatment section functions as a probe electrode portion. The ultrasonic probe is inserted through a sheath in a state in which the distal treatment section projects toward the distal direction. The jaw is attached to a distal portion of the sheath. The jaw is provided with an abutment portion which can abut on the distal treatment section in a state in which the jaw is closed relative to the distal treatment section. The abutment portion is formed of an insulative material. In addition, the jaw is provided with a jaw electrode portion which is formed of an electrically conductive material. A high-frequency current is transmitted to the jaw electrode portion through the sheath. In the state in which the abutment portion abuts on the distal treatment section, the jaw electrode portion does not come in contact with the distal treatment section. In the grasping treatment device, in the state in which a treatment target, such as a living tissue, is grasped between the distal treatment section and the jaw, the treatment target is treated by using the ultrasonic vibration and the high-frequency current.

BRIEF SUMMARY OF THE INVENTION

According to one aspect of the invention, a grasping treatment apparatus includes: a vibration transmission portion provided to extend along a center axis, and configured to transmit an ultrasonic vibration from a proximal direction to a distal direction; a distal treatment section provided in a distal portion of the vibration transmission portion, and configured to function as a probe electrode portion having a first electric potential by a high-frequency current being transmitted thereto; a jaw being openable and closable relative to the distal treatment section; a jaw electrode portion formed of an electrically conductive material in a part of the jaw, having a second electric potential different from the first electric potential by a high-frequency current being transmitted thereto, and including an electrode facing-surface which faces to the distal treatment section; an abutment portion formed of an insulative material in the jaw in a state in which the abutment portion is attached to the jaw electrode portion, being able to abut on the distal treatment section in a state in which the jaw is closed relative to the distal treatment section, and configured to space the distal treatment section and the jaw electrode portion apart from each other in a state in which the abutment portion abuts on the distal treatment section; a jaw insulation portion disposed in a part spaced apart from the abutment portion in a first width direction and a second width direction on the electrode facing-surface, when the first width direction is one side of a direction which is perpendicular to the center axis and is perpendicular to an opening direction and a closing direction of the jaw, and the second width direction is opposite to the first width direction, the jaw insulation portion being formed of an insulative material; and an insulation facing-surface provided on an outer surface of the jaw insulation portion, a spacing distance from the distal treatment section thereto being less than a distance from the electrode facing-surface to the distal treatment section in the state in which the abutment portion abuts on the distal treatment section.

According to one another aspect of the invention, a grasping unit which is openable and closable relative to a distal treatment section in a grasping treatment apparatus including a vibration transmission portion provided to extend along a center axis and configured to transmit an ultrasonic vibration from a proximal direction to a distal direction, the distal treatment section being provided in a distal portion of the vibration transmission portion and configured to function as a probe electrode portion having a first electric potential by a high-frequency current being transmitted thereto, the grasping unit including: a jaw electrode portion formed of an electrically conductive material, having a second electric potential different from the first electric potential by a high-frequency current being transmitted thereto, and including an electrode facing-surface which faces to the distal treatment section; an abutment portion formed of an insulative material in a state in which the abutment portion is attached to the jaw electrode portion, being able to abut on the distal treatment section in a state in which the grasping unit is closed relative to the distal treatment section, and configured to space the distal treatment section and the jaw electrode portion apart from each other in a state in which the abutment portion abuts on the distal treatment section; a jaw insulation portion disposed in a part spaced apart from the abutment portion in a first width direction and a second width direction on the electrode facing-surface, when the first width direction is one side of a direction which is perpendicular to the center axis and is perpendicular to an opening direction and a closing direction of the grasping unit, and the second width direction is opposite to the first width direction, the jaw insulation portion being formed of an insulative material; and an insulation facing-surface provided on an outer surface of the jaw insulation portion, a spacing distance from the distal treatment section thereto being less than a distance from the electrode facing-surface to the distal treatment section in the state in which the abutment portion abuts on the distal treatment section.

Advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

DETAILED DESCRIPTION OF THE INVENTION

First Embodiment

A first embodiment of the present invention is described with reference to FIG. 1 to FIG. 9.

Figure 1:
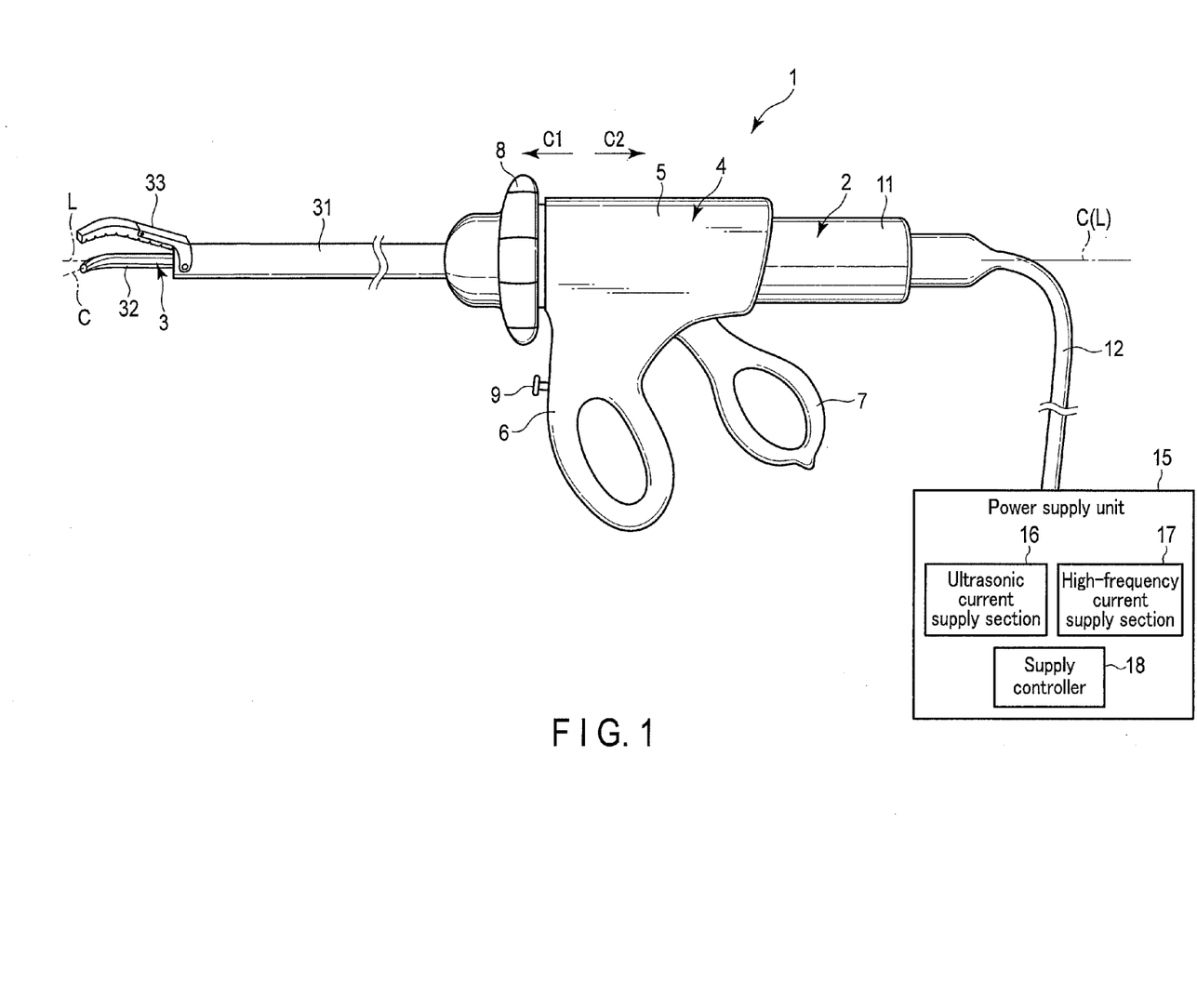
FIG. 1 is a schematic view illustrating a treatment system in which a grasping treatment apparatus according to a first embodiment is used.

FIG. 1 is a view illustrating a treatment system in which a grasping treatment apparatus 1 of the present embodiment is used. As illustrated in FIG. 1, the grasping treatment apparatus 1 has a longitudinal axis L which is parallel to a longitudinal direction. In addition, the grasping treatment apparatus 1 includes a vibrator unit 2, an ultrasonic probe 3, and a holding unit 4. Besides, the grasping treatment device 1 has a center axis C which passes through a center of the ultrasonic probe 3. One side of a direction, which is parallel to the center axis C, is a distal direction (direction of arrow C1 in FIG. 1), and the direction opposite to the distal direction is a proximal direction (direction of arrow C2 in FIG. 1). Additionally, the distal direction and proximal direction are referred to as an axis-parallel direction. In the present embodiment, the grasping treatment apparatus 1 is an ultrasonic coagulation-and-cutting apparatus which performs coagulation and cutting of a treatment target, such as a living tissue, by using an ultrasonic vibration. In addition, the grasping treatment apparatus 1 is a high-frequency treatment apparatus (bipolar treatment apparatus) which treats a treatment target by using a high-frequency current.

The holding unit 4 includes a cylindrical case portion 5 which is provided to extend along the center axis C (longitudinal axis L), a stationary handle 6 which is formed integral with the cylindrical case portion 5, and a movable handle 7 which is pivotably attached to the cylindrical case portion 5. The movable handle 7 pivots about a position of attachment to the cylindrical case portion 5, and thereby the movable handle 7 performs an opening motion or a closing motion relative to the stationary handle 6. In addition, the holding unit 4 includes a rotary operation knob 8 which is attached on the distal direction side of the cylindrical case portion 5. The rotary operation knob 8 is rotatable about the longitudinal axis L (center axis C) relative to the cylindrical case portion 5. Besides, an energy operation input button 9, which is an energy operation input section, is attached to the stationary handle 6.

The vibrator unit 2 includes a vibrator case 11. One end of a cable 12 is connected to a proximal portion of the transducer case 11. The other end of the cable 12 is connected to a power supply unit 15. The electric power supply unit 15 includes an ultrasonic current supply section 16, a high-frequency current supply section 17 and a supply controller 18. Here, the control unit 15 is an energy generator including, for example, a CPU (Central Processing Unit), an ASIC (Application Specification Integrated Circuit), etc. Besides, the ultrasonic current supply section 16 and high-frequency current supply section 17 are, for example, electric power supplies which are provided in the energy generator, and the energy controller 18 is constituted by, for example, an electronic circuit (control circuit) provided in a CPU, ASIC, etc.

Figure 2:
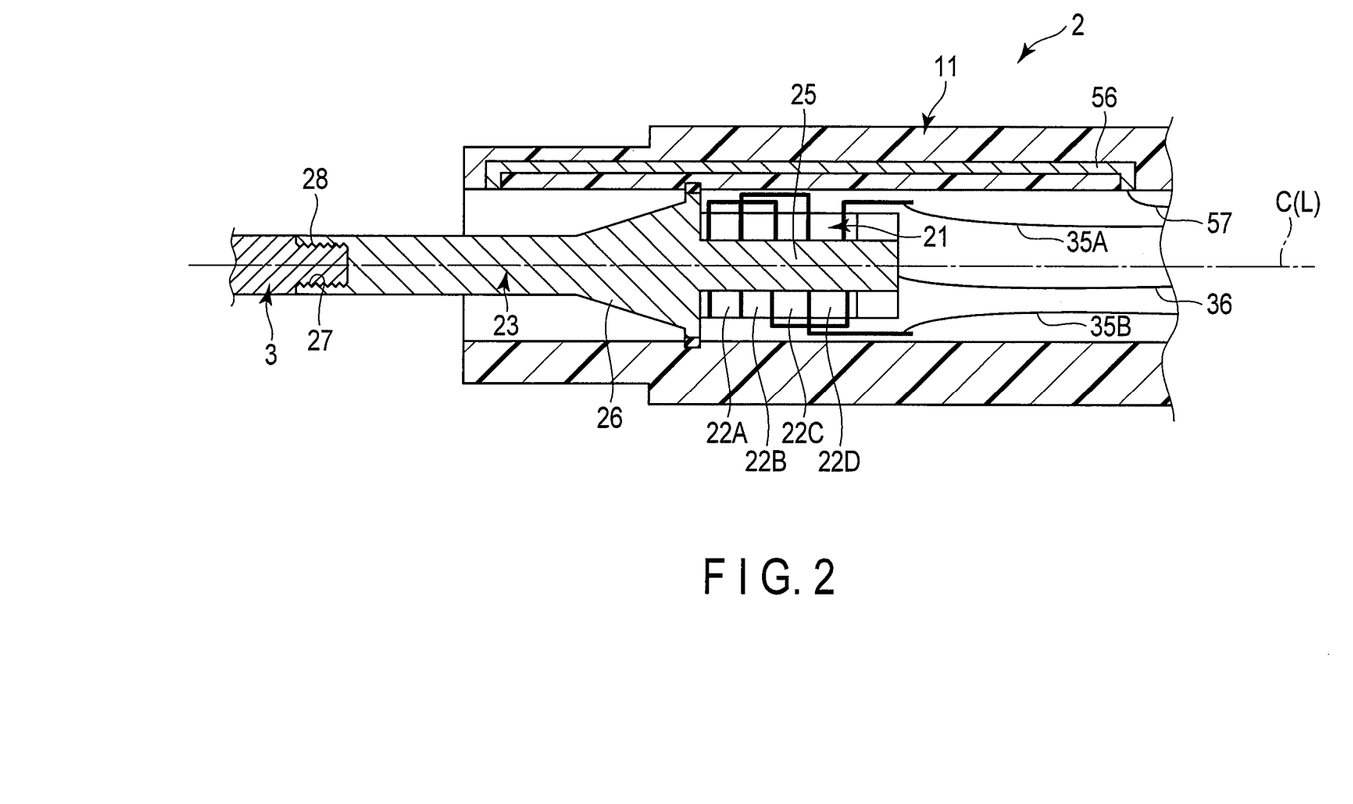
FIG. 2 is a cross-sectional view which schematically illustrates a structure of a vibrator unit according to the first embodiment.

FIG. 2 is a view illustrating the structure of the vibrator unit 2. As illustrated in FIG. 2, the transducer unit 2 includes an ultrasonic vibrator 21 which is an ultrasonic generation section configured to generate an ultrasonic vibration by being supplied with a current (electric power). The ultrasonic transducer 21 is provided inside the transducer case 11. The ultrasonic oscillator 21 includes a plurality of (four in this embodiment) piezoelectric elements 22A to 22D configured to convert a current (alternating current) to a vibration.

In addition, a horn member 23, which is provided to extend along the center axis C (longitudinal axis L), is provided inside the oscillator case 11. The horn member 23 includes a vibrator attachment portion 25. The members which form the ultrasonic vibrator 21, such as piezoelectric elements 22A to 22D, are attached to the transducer attachment portion 25. In addition, a cross-sectional area varying portion 26 is formed in the horn member 23. In the cross-sectional area varying portion 26, the cross-sectional area perpendicular to the center axis C (longitudinal axis L) decreases toward the distal direction. An amplitude of the ultrasonic vibration is increased by the cross-sectional area varying portion 26. A female screw portion 27 is provided in a distal portion of the horn member 23.

As illustrated in FIG. 2, a male screw portion 28 is provided in a proximal portion of the ultrasonic probe 3. The male screw portion 28 is engaged with the female screw portion 27, and thereby the ultrasonic probe 3 is connected to the distal direction side of the horn member 23. The ultrasonic probe 3 is provided to extend along the center axis C.

As illustrated in FIG. 1, the ultrasonic probe 3 is inserted through a sheath 31. A distal treatment section 32 is provided in a distal portion of the ultrasonic probe 3. The ultrasonic probe 3 is inserted through the sheath 31 in the state in which the distal treatment section 32 projects from a distal end of the sheath 31 toward the distal direction. A jaw 33, which is a grasping unit, is pivotably attached to the distal portion of the sheath 31. The jaw 33 pivots relative to the sheath 31, and thereby the jaw 33 performs an opening motion or a closing motion relative to the distal treatment section 32.

As illustrated in FIG. 2, one end of each of electric wiring lines 35A, 35B is connected to the ultrasonic transducer 21. The electric wiring lines 35A, 35B extend through an inside of the cable 12, and the other end each thereof is connected to the ultrasonic current supply section 16 of the power supply unit 15. An ultrasonic generation current is supplied from the ultrasonic current supply section 16 to the ultrasonic vibrator 21 via the electric wiring lines 35A, 35B, and thereby an ultrasonic vibration occurs in the ultrasonic oscillator 21. Then, the generated ultrasonic vibration is transmitted from the ultrasonic vibrator 21 to the ultrasonic probe 3 via the horn member 23. In addition, in the ultrasonic probe 3, the ultrasonic vibration is transmitted to the distal treatment section 32 from the proximal direction toward the distal direction. Specifically, the ultrasonic probe 3 serves as a vibration transmission portion configured to transmit the ultrasonic vibration from the proximal direction toward the distal direction. Using the transmitted ultrasonic vibration, the distal treatment section 32 performs treatment of a treatment target such as a living body tissue. Incidentally, by transmitting the ultrasonic vibration, the ultrasonic probe 3 performs a longitudinal vibration, a vibration direction of which is parallel to the center axis C, in a predetermined vibration mode that is used at the time of treatment. In addition, a distal end of the ultrasonic probe 3 (a distal end of distal treatment section 32) is a most-distal antinode position A1 that is one of antinode positions of the longitudinal vibration. The most-distal antinode position A1 is an antinode position located most distally among the antinode positions of the longitudinal vibration. Specifically, a resonance frequency is adjusted in a state that the ultrasonic probe 3 vibrates in the predetermined vibration mode in which the most-distal antinode position A1 is located at the distal end of the ultrasonic probe 3. In addition, in the predetermined vibration mode, a proximal end the horn member 23 and the distal end of the ultrasonic probe 3 are antinode positions, and there is at least one node position of the longitudinal vibration between the proximal end of the horn member 23 and ultrasonic probe 3.

One end of an electric wiring line 36 is connected to the horn member 23. The electric wiring line 36 extends through the inside of the cable 12, and the other end thereof is connected to the high-frequency current supply section 17 of the power supply unit 15. Thereby, a probe-side current path of a high-frequency current, which is supplied from the high-frequency current supply section 17, is formed up to the distal treatment section 32 from the high-frequency current supply section 17 via the electric wiring line 36, horn member 23 and ultrasonic probe 3. The high-frequency current is transmitted through the probe-side current path, and thereby the distal treatment unit 32 functions as a probe-side electrode portion having a first electric potential E1.

Figure 3:
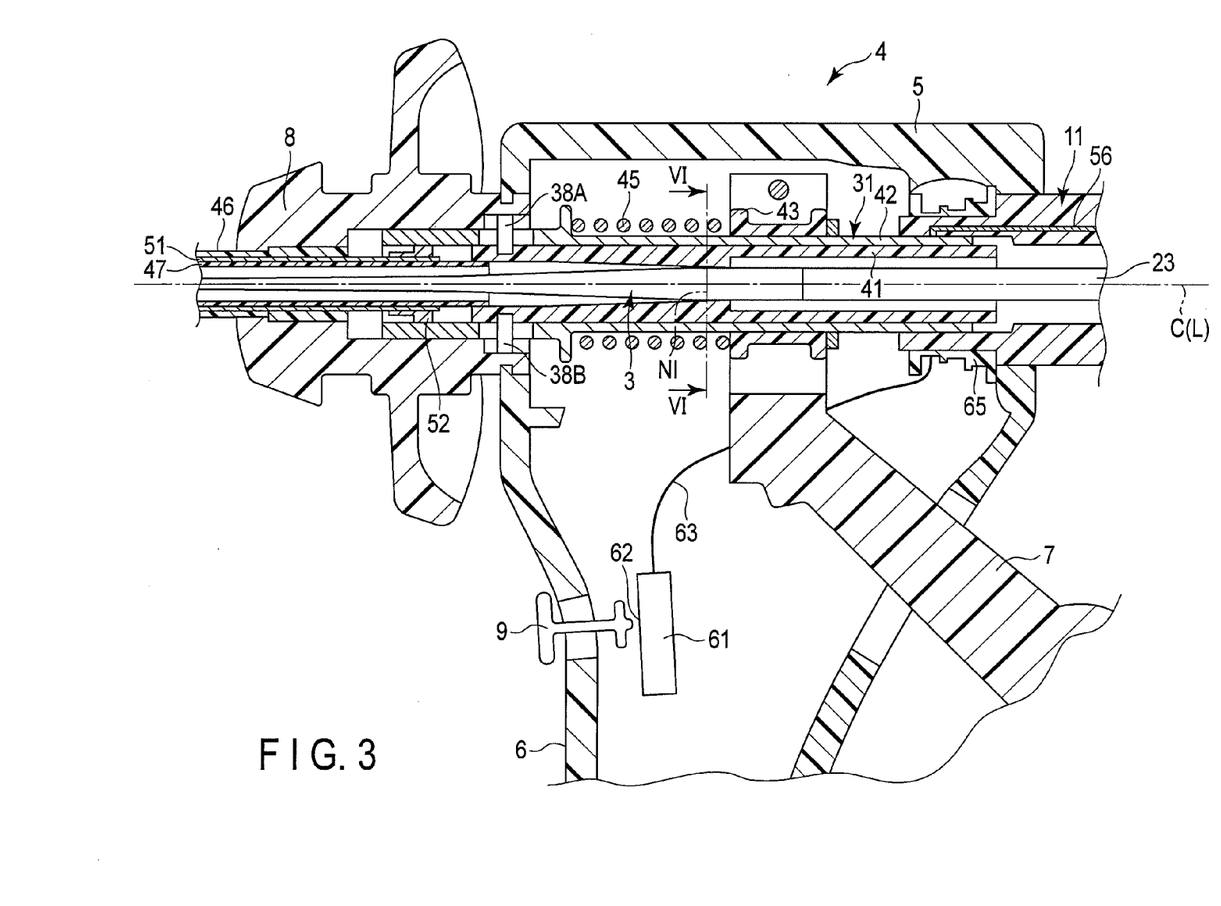
FIG. 3 is a cross-sectional view which schematically illustrates an internal structure of a holding unit according to the first embodiment.

FIG. 3 is a view illustrating an internal structure of the holding unit 4. As illustrated in FIG. 3, the sheath 31 and the ultrasonic probe 3 are inserted in the inside of the cylindrical case portion 5 from the distal direction side, and the vibrator unit 2 is inserted in the inside of the cylindrical case portion 5 from the proximal direction side. Then, in the inside of the cylindrical case portion 5, the proximal portion of the sheath 31 is coupled to the distal portion of the vibrator case 11. In addition, in the inside of the cylindrical case portion 5, the ultrasonic probe 3 is connected to the horn member 23.

Here, a direction away from the center axis C is referred to as an outer peripheral direction (abaxial direction), and a direction toward the center axis C is referred to as an inner peripheral direction (adaxial direction). In addition, the outer peripheral direction and the inner peripheral direction are referred to as a radial direction. The sheath 31 includes a stationary cylindrical member 41 which is fixed to the rotary operation knob 8 via engaging pins 38A, 38B, and a movable cylindrical member 42 which is movable along the center axis C (longitudinal axis L) relative to the cylindrical case portion 5, rotary operation knob 8 and stationary cylindrical member 41. The movable cylindrical member 42 is provided on the outer peripheral direction side of the stationary cylindrical member 41, and is coupled to the rotary operation knob 8 via the engaging pins 38A, 38B. In addition, the stationary cylindrical member 41 is formed of an insulative material, and the movable cylindrical member 42 is formed of an electrically conductive material. The movable cylindrical member 42 is restricted in such a state that the movable cylindrical member 42 is movable along the center axis C relative to the rotary operation knob 8, but is unrotatable about the longitudinal axis L relative to the rotary operation knob 8. Because of the above-described structure, the stationary cylindrical member 41 and the movable cylindrical member 42 are rotatable, integral with the rotary operation knob 8, about the longitudinal axis L (center axis C) relative to the cylindrical case portion 5.

The movable cylindrical member 42 is engaged with the vibrator case 11 between the sheath 31 and the vibrator case 11, in the state in which the movable cylindrical member 42 is inserted in the vibrator case 11. Thereby, the sheath 31 is coupled to the transducer case 11. The movable cylindrical member 42 and the vibrator case 11 are restricted in the state in which the movable cylindrical member 42 and oscillator case 11 do not rotate about the longitudinal axis L relative to each other. However, the movable cylindrical member 42 is movable along the center axis C (longitudinal axis L) relative to the vibrator case 11.

A slider member 43, which is formed of an insulative material, is provided on the outer peripheral direction side (abaxial direction side) with respect to the movable cylindrical member 42. The slider member 43 is disposed on an outer peripheral surface of the movable cylindrical member 42. The movable handle 7 is attached to the slider member 43. In addition, a coil spring 45 is provided on the outer peripheral direction side with respect to the movable cylindrical member 42. A proximal end of the coil spring 45 is connected to the slider member 43, and a distal end of the coil spring 45 is connected to the movable cylindrical member 42. The coil spring 45 is provided to extend between the slider member 43 and the movable cylindrical member 42 in a state in which the coil spring 45 contracts by a certain contraction amount from a natural state. By causing the movable handle 7 to perform an opening motion or a closing motion relative to the stationary handle 6, the operation force by the movable handle 7 is transmitted to the movable cylindrical member 42 via the slider member 43 and coil spring 45. Thereby, the movable cylindrical member 42 moves along the center axis C relative to the ultrasonic probe 3 and the holding unit 4.

The sheath 31 includes an outer tube 46 which is fixed to a distal end of the stationary cylindrical member 41, and an inner tube 47 which is provided on the inner peripheral direction side (adaxial direction side) with respect to the outer tube 46. The inner tube 47 is fixed to a distal portion of the stationary cylindrical member 41. Since the outer tube 46 and inner tube 47 are fixed with respect to the stationary cylindrical member 41, the outer tube 46 and inner tube 47 are rotatable, together with the rotary operation knob 8, about the longitudinal axis L (center axis C) relative to the cylindrical case portion 5.

In addition, the sheath 31 includes a movable pipe 51 which is fixed to a distal portion of the movable cylindrical member 42. The movable pipe 51 is provided to extend along the center axis C (longitudinal axis L) between the outer tube 46 and inner tube 47 in the radial direction (inner peripheral direction and outer peripheral direction). The movable pipe 51 is fixed with respect to the movable cylindrical member 42 via a connection member 52. In addition, the movable pipe 51 is formed of an electrically conductive material. The movable cylindrical member 42 moves along the center axis C by the transmission of the operation force by the movable handle 7. Thereby, the movable pipe 51, as one piece with the movable cylindrical member 42, moves along the center axis C (longitudinal axis L) relative to the ultrasonic probe 3 and the holding unit 4.

Figure 4:
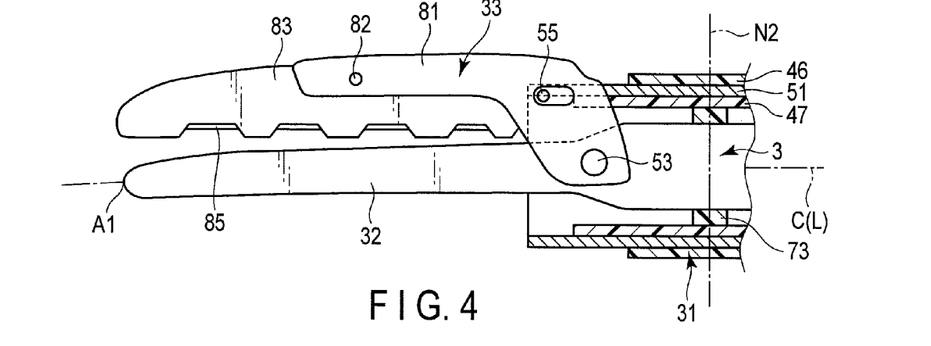
FIG. 4 is a schematic view illustrating a structure of a distal portion of the grasping treatment apparatus according to the first embodiment.
Figure 5:
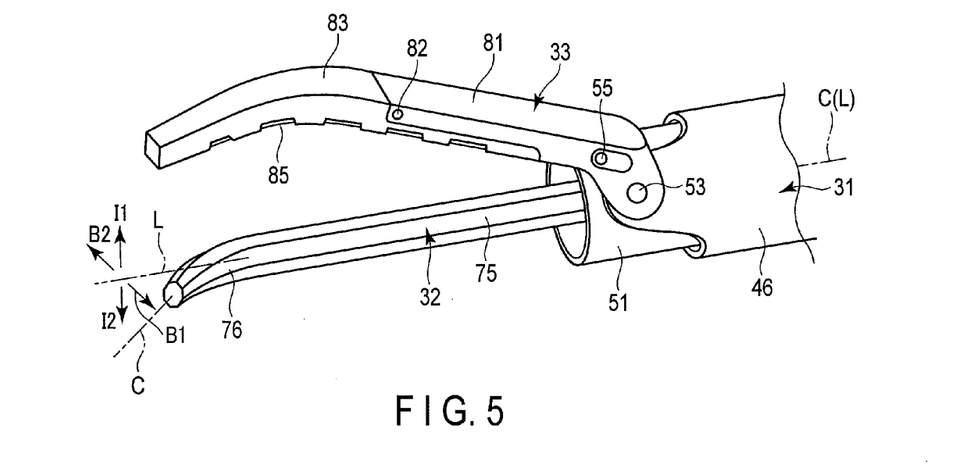
FIG. 5 is a perspective view which schematically illustrates the structure of the distal portion of the grasping treatment apparatus according to the first embodiment.

FIG. 4 and FIG. 5 are views illustrating a structure of a distal portion of the grasping treatment apparatus 1. As illustrated in FIG. 4 and FIG. 5, the outer tube 46, inner tube 47 and movable pipe 51 are provided to extend up to the distal portion of the sheath 31. The jaw 33, which is the grasping unit, is coupled to the outer tube 46 via a coupling pin 53. In addition, a distal portion of the movable pipe 51 is connected to the jaw 33 via a connection pin 55. The movable cylindrical member 42 and movable pipe 51 move along the center axis C (longitudinal axis L), whereby the jaw 33 turns about the coupling pin 53. Thereby, the jaw 33 performs an opening motion or a closing motion relative to the distal treatment section 32. By closing the jaw 33 relative to the distal treatment section 32, a treatment target, such as a living tissue, is grasped between the jaw 33 and distal treatment section 32.

As illustrated in FIG. 2, a conductive portion 56 is formed in the vibrator case 11. One end of an electric wiring line 57 is connected to the conductive portion 56. The electric wiring line 57 extends through the inside of the cable 12, and the other end thereof is connected to the high-frequency current supply section 17 of the electric power supply unit 15. In addition, in the state in which the vibrator case 11 is coupled to the sheath 31, the movable cylindrical member 42 of the sheath 31 is in contact with the conductive portion 56 of the oscillator case 11, and the movable cylindrical member 42 is electrically connected to the conductive portion 56 of the vibrator case 11. Thereby, a jaw-side current path of the high-frequency current, which is supplied from the high-frequency current supply section 17, is formed up to the jaw 33 from the high-frequency current supply section 17 via the electric wiring line 57, conductive portion 56 of vibrator case 11, movable cylindrical member 42, and movable pipe 51.

The supply controller 18 is configured to control, based on an input of an energy operation in the energy operation input button 9, a supply state of an ultrasonic generation current from the ultrasonic current supply section 16 and a supply state of a high-frequency current from the high-frequency current supply section 17. As illustrated in FIG. 3, an electric circuit board 61 is provided inside the stationary handle 6. In addition, a switch 62 is provided on the electric circuit board 61. The switch 62 is closed by pressing the energy operation input button 9 and thereby inputting the energy operation. One end of an electric signal line 63 is connected to the switch 62. In addition, an electrical connection ring 65 is fixed to an inner peripheral surface of the cylindrical case portion 5. The other end of the electric signal line 63 is connected to a conductive portion (not shown) of the electrical connection ring 65. The switch 62 is electrically connected to the supply controller 18 via an electric signal path which is formed from the electric signal line 63, the conductive portion of electrical connection ring 65, etc. By the switch 62 being closed, an electric signal is transmitted to the supply controller 18, and the input of the energy operation is detected. By the input of the energy operation being detected, an ultrasonic generation current is supplied from the ultrasonic current supply section 16 and a high-frequency current is supplied from the high-frequency current supply section 17.

Figure 6:
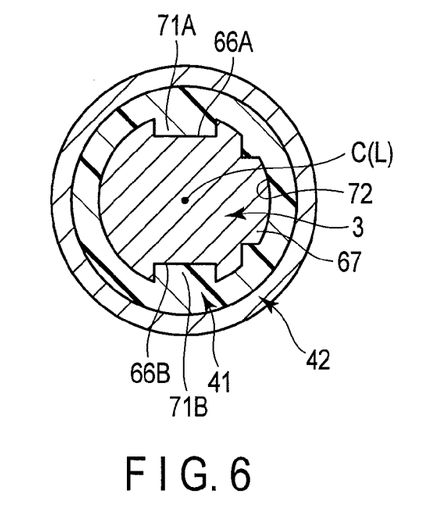
FIG. 6 is a cross-sectional view taken along line VI-VI in FIG. 3.

As illustrated in FIG. 3, the ultrasonic probe 3 is fixed to the stationary cylindrical member 41 of the sheath 31 at a fixed node position N1 that is one of node positions of the longitudinal vibration in the above-described predetermined vibration mode. The fixed node position N1 is located at the proximal portion of the ultrasonic probe 3. FIG. 6 is a cross-sectional view taken along line VI-VI in FIG. 3, and illustrates, in a cross section perpendicular to the center axis C (longitudinal axis L), the ultrasonic probe 3 and sheath 31 at the fixed node position N1. As illustrated in FIG. 6, the ultrasonic probe 3 is provided with engaging grooves 66A and 66B and an engaging projection 67 at position corresponding to the fixed node position N1 in the axis-parallel direction which is parallel to the center axis C. In addition, the stationary cylindrical member 41 of the sheath 31 is provided with engaging projections 71A and 71B and an engaging groove 72 at position corresponding to the engaging grooves 66A and 66B and engaging projection 67 in the axis-parallel direction. The engaging projection 71A is engaged in the engaging groove 66A, the engaging projection 71B is engaged in the engaging groove 66B, and the engaging projection 67 is engaged in the engaging groove 72, and thereby the ultrasonic probe 3 is fixed to the stationary cylindrical member 41 at the fixed node position N1.

As illustrated in FIG. 4, at a most-distal node position N2 that is one of node positions of the longitudinal vibration in the above-described predetermined vibration mode, a support member 73, which is formed of an insulative material, is provided between the ultrasonic probe 3 and sheath 31. The most-distal node position N2 is a node position which is located most distally among the node positions of the longitudinal vibration in the predetermined vibration mode.

By the support member 73, the ultrasonic probe 3 is supported with respect to the sheath 31. In addition, also at node positions of the longitudinal vibration other than the fixed node position N1 and foremost distal node position N2, the ultrasonic probe 3 is supported with respect to the sheath 31 by a support member (not shown) which is similar to the support member 73. Here, at positions other than the node positions of the longitudinal vibration, the ultrasonic probe 3 is not fixed with respect to the sheath 31, and is not supported with respect to the sheath 31. Since the ultrasonic probe 3 is fixed or supported with respect to the sheath 31 at only the node positions of the longitudinal vibration at which the amplitude is zero, the ultrasonic probe 3 properly performs the longitudinal vibration by transmitting the ultrasonic vibration.

As illustrated in FIG. 5, the distal treatment section 32 includes a coaxial extension portion 75 which is provided to extend in the state in which the center axis C is coaxial with the longitudinal axis L. Here, one side of a direction, which is perpendicular to the center axis C and is perpendicular to an opening direction (direction of arrow 11 in FIG. 5) and a closing direction (direction of arrow 12 in FIG. 5) of the jaw 33, is referred to as a first width direction (direction of arrow B1 in FIG. 5), and a opposite side of the first width direction is referred to as a second width direction (direction of arrow B2 in FIG. 5). The distal treatment section 32 includes a bend extension portion 76 in which the center axis C bends from the second width direction toward the first width direction relative to the longitudinal axis L. The bend extension portion 76 is continuous to the distal direction side of the coaxial extension portion 75. At the time of treatment, by the provision of the bend extension portion 76, the visibility of the treatment target, which is grasped between the distal treatment section 32 and jaw 22, is secured. In addition, by the provision of the bend extension portion 76, the center of gravity of the distal treatment unit 32 is located on the first width direction side with respect to the longitudinal axis L. Incidentally, the center axis C, which passes through the center of the horn member 23 and the center of the ultrasonic probe 3, is coaxial with the longitudinal axis L at parts other than the bend extension portion 76.

As illustrated in FIG. 4 and FIG. 5, the jaw 33 includes a jaw body 81 which is formed of an electrically conductive material, and a jaw electrode portion 83 which is attached to the jaw body 81 via a connection pin 82. A proximal portion of the jaw body 81 is attached to the distal portion of the sheath 31. The jaw electrode portion 83 is formed of an electrically conductive material. A pad member 85, which is formed of an insulative material, is attached to the jaw electrode unit 83. A high-frequency current, which is transmitted to the jaw 33 via the jaw-side current path, is transmitted to the jaw electrode portion 83 via the jaw body 81 and connection pin 82. By the high-frequency current being transmitted to the jaw electrode portion 83, the jaw electrode portion 83 has a second electric potential E2 which is different from the first electric potential E1.

Figure 7:
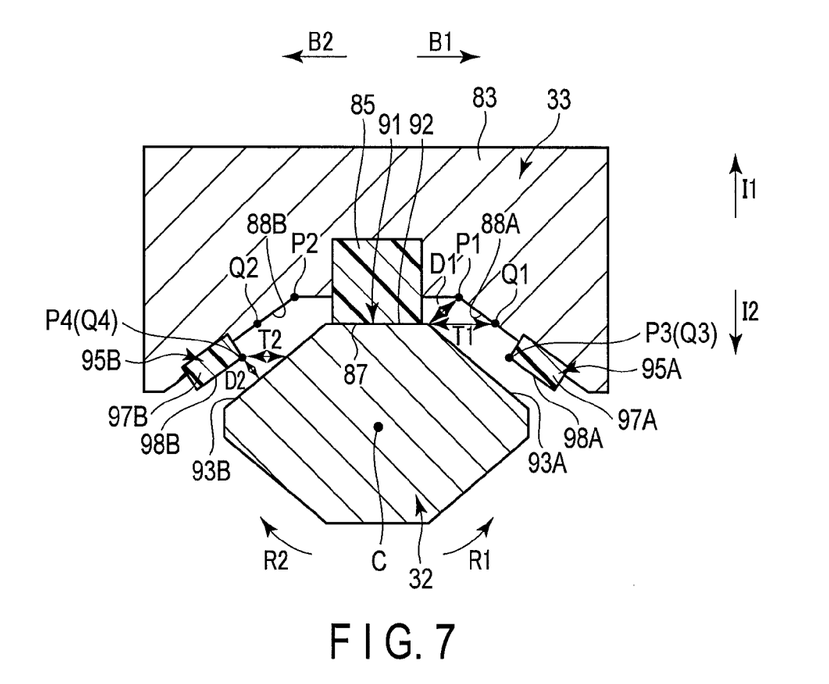
FIG. 7 is a cross-sectional view which schematically illustrates, in a cross section perpendicular to a center axis, a jaw and a distal treatment section according to the first embodiment.

FIG. 7 is a view illustrating, in a cross section perpendicular to the center axis C, the distal treatment section 32 and jaw 33. Here, in FIG. 7, in the state in which there is no treatment target between the jaw 33 and distal treatment section 32, the jaw 33 is closed relative to the distal treatment section 32. As illustrated in FIG. 7, the jaw 33 is closed relative to the distal treatment section 32 in the state in which there is no treatment target between the jaw 33 and distal treatment section 32, and thereby an abutment portion 87 of the pad member 85 abuts on the distal treatment section 32. Specifically, in the pad member 85 of the jaw 33, the abutment portion 87, which can abut on the distal treatment section 32 in the state in which the jaw 33 is closed relative to the distal treatment section 32, is formed as a part of the jaw 33. Incidentally, in the present embodiment, the cross section of the distal treatment section 32, which is perpendicular to the center axis C, is formed in a substantially octagonal shape.

The distal treatment section 32 includes a treatment section facing-surface 91 which faces to the jaw 33. The treatment section opposed-surface 91 includes a receiving surface 92 on which the abutment portion 87 of the pad member 85 abuts, and inclined surfaces 93A and 93B which are inclined with respect to the receiving surface 92. The inclined surface 93A is continuous to the first width direction side (direction side of arrow B1 in FIG. 7) of the receiving surface 92, and the inclined surface 93B is continuous with the second width direction side (direction side of arrow B2 in FIG. 7) of the receiving surface 92.

The jaw electrode portion 83 does not come in contact with the distal treatment section 32 in the state in which the abutment portion 87 abuts on the receiving surface 92 of the distal treatment section 32. The jaw electrode portion 83 includes an electrode facing-surface 88A which faces to the inclined surface 93A of the distal treatment section 32, and an electrode facing-surface 88B which is opposed to the inclined surface 93B of the distal treatment section 32. In the state in which the abutment portion 87 abuts on the distal treatment section 32, the electrode facing-surfaces 88A and 88B are spaced apart from the distal treatment section 32 and faces to the distal treatment section 32.

Each electrode opposed-surface 88A, 88B is formed in a planar shape. However, the electrode facing-surface 88A is not parallel to the inclined surface 93A, and the electrode facing-surface 88B is not parallel to the inclined surface 93B. Thus, in each electrode facing-surface 88A or 88B, the spacing distance from the distal treatment section 32 varies in accordance with positions therein. On each of the electrode opposed-surfaces 88A, 88B, the position, at which the spacing distance from the distal treatment section 32 in the state in which the abutment portion 87 abuts on the distal treatment section 32 becomes minimum, is referred to as an electrode minimum spacing position (P1 or P2). In the state in which the abutment portion 87 abuts on the distal treatment section 32, the spacing distance from the distal treatment section 32 becomes a dimension D1 at the electrode minimum spacing position (P1 or P2) of each electrode counter-surface 88A or 88B.

In addition, the dimension between the distal treatment section 32 and jaw 33 in the first width direction and second width direction is referred to as a width-directional spacing dimension. The dimension in the first width direction from the inclined surface 93A of the distal treatment section 32 in the electrode facing-surface 88A, and the dimension in the second width direction from the inclined surface 93B of the distal treatment section 32 in the electrode facing-surface 88B, is indicated by the width-directional spacing dimension. Since the electrode opposed-surface 88A is not parallel to the inclined surface 93A and the electrode opposed-surface 88B is not parallel to the inclined surface 93B, the width-directional spacing dimension from the distal treatment section 32, like the spacing distance from the distal treatment section 32, varies in each electrode facing-surface 88A or 88B in accordance with positions therein. On each of the electrode facing-surfaces 88A, 88B, the position, at which the width-directional spacing dimension from the distal treatment section 32 in the state in which the abutment portion 87 abuts on the distal treatment section 32 becomes minimum, is referred to as an electrode minimum width-directional spacing position (Q1 or Q2). In the state in which the abutment portion 87 abuts on the distal treatment section 32, the width-directional spacing dimension from the distal treatment section 32 becomes a dimension T1 at the electrode minimum width-directional spacing position (Q1 or Q2) of each electrode facing-surface 88A or 88B.

Besides, jaw insulation portions 95A and 95B, which are formed of an insulative material, are attached to the jaw electrode portion 83. The jaw insulation portion 95A is formed at a position spaced apart from the abutment portion 87 in the first width direction, and the jaw insulation portions 95B is formed at a position spaced apart from the abutment portion 87 in the second width direction. In other words, the jaw insulation portions 95A and 95B are provided at positions spaced apart from the abutment portion 87 in the first width direction and second width direction. Accordingly, each jaw insulation portion 95A or 95B and the abutment portion 87 are not continuous, and the jaw electrode unit 83, which is formed of an electrically conductive material, is provided between each jaw insulation portion 95A or 95B and the abutment portion 87. In addition, the jaw insulation portion 95A is located on the first width direction side with respect to the center axis C, and the jaw insulation portion 95B is located on the second width direction side with respect to the center axis C.

In the state in which the abutment portion 87 abuts on the receiving surface 92 of the distal treatment section 32, the jaw insulation portion 95A, 95B does not come in contact with the distal treatment section 32. The jaw insulation portion 95A includes an insulation projection portion 97A which projects from the electrode facing-surface 88A toward the inclined surface 93A of the distal treatment section 32, and the jaw insulation portion 95B includes an insulation projection portion 97B which projects from the electrode facing-surface 88B toward the inclined surface 93B of the distal treatment section 32. The insulation projection portion 97A includes an insulation facing-surface 98A which faces to the inclined surface 93A of the distal treatment section 32, and the insulation projection portion 97B includes an insulation facing-surface 98B which is opposed to the inclined surface 93B of the distal treatment section 32. In the state in which the abutment portion 87 abuts on the distal treatment section 32, the insulation facing-surfaces 98A and 98B are spaced apart from the distal treatment section 32 and faces to the distal treatment section 32.

Each insulation opposed-surface 98A or 98B is formed in a planar shape. However, the insulation facing-surface 98A is not parallel to the inclined surface 93A, and the insulation facing-surface 98B is not parallel to the inclined surface 93B. Thus, in each of the insulation opposed-surfaces 98A, 98B, the spacing distance from the distal treatment section 32 varies in accordance with positions therein. On each insulation facing-surface 98A or 98B, the position, at which the spacing distance from the distal treatment section 32 in the state in which the abutment portion 87 abuts on the distal treatment section 32 becomes minimum, is referred to as an insulation minimum spacing position (P3 or P4). In the state in which the abutment portion 87 abuts on the distal treatment section 32, the spacing distance from the distal treatment section 32 becomes a dimension D2 at the insulation minimum spacing position (P3 or P4) of each insulation facing-surface 98A or 98B. The dimension D2 of the spacing distance from the distal treatment section 32 at the insulation minimum spacing position (P3 or P4) of each of the insulation facing-surfaces 98A, 98B becomes less than the dimension D1 of the spacing distance from the distal treatment section 32 at the electrode minimum spacing position (P1 or P2) of each of the electrode facing-surfaces 88A, 88B. Accordingly, in the state in which the abutment portion 87 abuts on the distal treatment section 32, at least a part of each of the insulation facing-surfaces 98A, 98B has a less spacing distance from the distal treatment section 32 than any positions of the electrode facing-surfaces 88A, 88B.

The dimension in the first width direction from the inclined surface 93A of the distal treatment section 32 at the insulation facing-surface 98A, and the dimension in the second width direction from the inclined surface 93B of the distal treatment section 32 at the insulation facing-surface 98B, are indicated by the width-directional spacing dimension. Since the insulation opposed-surface 98A is not parallel to the inclined surface 93A and the insulation opposed-surface 98B is not parallel to the inclined surface 93B, the width-directional spacing dimension from the distal treatment section 32, like the spacing distance from the distal treatment section 32, varies in each of the insulation facing-surfaces 98A, 98B in accordance with positions therein. On each insulation facing-surface 98A or 98B, the position, at which the width-directional spacing dimension from the distal treatment section 32 in the state in which the abutment portion 87 abuts on the distal treatment section 32 becomes minimum, is referred to as an insulation minimum width-directional spacing position (Q3 or Q4). In the state in which the abutment portion 87 abuts on the distal treatment section 32, the width-directional spacing dimension from the distal treatment section 32 becomes a dimension T2 at the insulation minimum width-directional spacing position (Q3 or Q4) of each insulation facing-surface 98A or 98B. The dimension T2 of the width-directional spacing dimension from the distal treatment section 32 at the insulation minimum spacing position (Q3 or Q4) of each of the insulation facing-surfaces 98A, 98B becomes less than the dimension T1 of the width-directional spacing dimension from the distal treatment section 32 at the electrode minimum width-directional spacing position (Q1 or Q2) of each of the electrode acing-surfaces 88A, 88B. Accordingly, in the state in which the abutment portion 87 abuts on the distal treatment section 32, at least a part of each of the insulation facing-surfaces 98A, 98B has a less width-directional spacing dimension from the distal treatment section 32 in the first width direction and second width direction than any positions of the electrode facing-surface 88A, 88B.

Next, the function and advantageous effects of the grasping treatment apparatus 1 of the present embodiment are described. When a treatment target, such as a living tissue, is treated by using the grasping treatment apparatus 1, the ultrasonic probe 3, sheath 31 and jaw 33 is inserted into a body cavity. Then, in the state in which the treatment target is positioned between the jaw 33 and distal treatment section 32, the movable handle 7 is closed relative to the stationary handle 6. Thereby, the movable cylindrical member 42 and movable pipe 51 move along the center axis C, and the jaw 33 performs a closing motion relative to the distal treatment section 32. Thereby, the treatment target is grasped between the jaw 33 and distal treatment section 32.

Then, by the energy operation being input in the energy operation input button 9, an ultrasonic generation current is supplied from the ultrasonic current supply section 16 to the ultrasonic vibrator 21, and a high-frequency current is supplied from the high-frequency current supply section 17 to the probe-side current path and jaw-side current path. By the ultrasonic generation current being supplied to the ultrasonic oscillator 21, an ultrasonic vibration occur in the ultrasonic vibrator 21. The generated ultrasonic vibration is propagated to the distal treatment section 32 via the horn member 23 and ultrasonic probe 3, and the probe 3 and horn member 23 longitudinally vibrate in a predetermined vibration mode. Since the distal treatment section 32 longitudinally vibrates in the state in which the treatment target is grasped between the jaw 33 and distal treatment section 32, a frictional heat occurs between the distal treatment section 32 and the treatment target. By the frictional heat, the treatment target is coagulated and, at the same time, is cut. In addition, a high-frequency electric power is transmitted to the distal treatment section (probe electrode portion) 32 via the probe-side current path, and a high-frequency electric power is transmitted to the jaw electrode portion 83 of the jaw 33 via the jaw-side current path. Thus, in the state in which the treatment target is grasped between the distal treatment section 32 and jaw 33, a high-frequency current flows through the treatment target between the distal treatment section 32 and the jaw electrode portion 83. Thereby, the treatment target is denatured, and a coagulation of the treatment target is facilitated.

Here, in the predetermined vibration mode, the ultrasonic probe 3 is fixed or supported with respect to the sheath 31 at only node positions of the longitudinal vibration. In addition, the fixed node position N1, at which the ultrasonic probe 3 is fixed to the sheath 31, is located in the proximal portion of the ultrasonic probe 3 in the axis-parallel direction. The most-distal node position N2, which is located most distally among the support positions of the ultrasonic probe 3 with respect to the sheath 31, is located inside the sheath 31. Because of this structure, the distal treatment section 32, which is located in the distal portion of the ultrasonic probe 3 and projects from the sheath 31 toward the distal direction, is located spaced apart in the axis-parallel direction from each node position at which the ultrasonic probe 3 is fixed or supported with respect to the sheath 31. Thus, the distal treatment section 32 is not firmly fixed with respect to the sheath 31. In the state in which the treatment target is grasped between the distal treatment section 32 and jaw 33, a pushing force acts on the distal treatment section 32 from the jaw 33. Since the distal treatment section 32 is not firmly fixed to the sheath 31, there is such a case that the distal treatment section 32 twists around the center axis C, or moves relative to the jaw 33 in the first width direction and second width direction, by the pushing force from the jaw 33.

Figure 8:
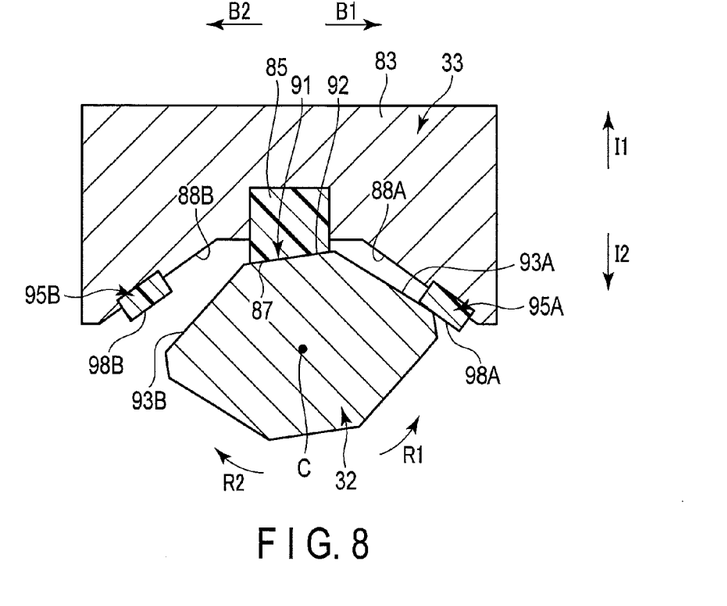
FIG. 8 is a cross-sectional view which schematically illustrates a state in which the distal treatment section according to the first embodiment has twisted about the center axis toward a first twist direction from a state shown in FIG. 7.

FIG. 8 is a view illustrating a state in which the distal treatment section 32 has twisted about the center axis C in a first twist direction (direction of arrow R1 in FIG. 8) from the state (state of FIG. 7) in which the jaw 33 abuts on the receiving surface 92 of the distal treatment section 32. FIG. 8 illustrates the jaw 33 and distal treatment section 32 in a cross section perpendicular to the center axis C. Here, by the twisting of the distal treatment section 32 toward the first twist direction, the distal treatment section 32 twists from the state in which the jaw 33 abuts on the receiving surface 92 of the distal treatment section 32 to the state in which the inclined surface 93A moves toward the jaw 33. On the other hand, by the twisting of the distal treatment section 32 in the second twist direction (direction of arrow R2 in FIG. 8), the distal treatment section 32 twists from the state in which the jaw 33 abuts on the receiving surface 92 of the distal treatment section 32 to the state in which the inclined surface 93B moves toward the jaw 33.

As illustrated in FIG. 8, when the distal treatment section 32 has twisted in the first twist direction from the state (state of FIG. 7) in which the jaw 33 abuts on the receiving surface 92 of the distal treatment section 32, the inclined surface 93A of the distal treatment section 32 abuts on the insulation facing-surface 98A of the jaw insulation portion 95A. The dimension D2 of the spacing distance from the distal treatment section 32 at the insulation minimum spacing position P3 of the insulation facing-surface 98A becomes less than the dimension D1 of the spacing distance from the distal treatment section 32 at the electrode minimum spacing position P1 of the electrode facing-surface 88A. Accordingly, in the state in which the abutment portion 87 abuts on the distal treatment section 32, at least a part of the insulation facing-surface 98A has a less spacing distance from the distal treatment section 32 than any positions of the electrode facing-surface 88A. Therefore, in the state in which the distal treatment section 32 abuts on the insulation facing-surface 98A of the jaw insulation portion 95A by the twisting of the distal treatment section 32 in the first twist direction, the electrode facing-surface 88A of the jaw electrode section 83 is spaced apart, at any position, from the distal treatment section 32.

On the other hand, when the distal treatment section 32 has twisted in the second twist direction from the state (state of FIG. 7) in which the jaw 33 abuts on the receiving surface 92 of the distal treatment section 32, the inclined surface 93B of the distal treatment section 32 abuts on the insulation facing-surface 98B of the jaw insulation portion 95B. In addition, in the state in which the distal treatment section 32 abuts on the insulation facing-surface 98B of the jaw insulation portion 95B by the twisting of the distal treatment section 32 in the second twist direction, the electrode facing-surface 88B of the jaw electrode portion 83 is spaced apart, at any position, from the distal treatment section 32.

As has been described above, in the treatment of the treatment target grasped between the jaw 33 and distal treatment section 32, even when the distal treatment section 32 has twisted due to the pushing force from the jaw 33, the distal treatment section 32 abuts on the insulation opposed-surface 98A of the jaw insulation portion 95A or the insulation opposed-surface 98B of the jaw insulation portion 95B. Thereby, even when the distal treatment section 32 has twisted, it is possible to prevent the distal treatment section 32, which functions as the probe-side electrode portion and which performs the longitudinal vibration, from coming in contact with the jaw electrode portion 83. Thereby, the occurrence of a spark due to the contact of the distal treatment section 32 with the jaw electrode portion 83 can effectively be prevented, and the occurrence of a crack in the distal treatment section 32 can effectively be prevented.

Figure 9:
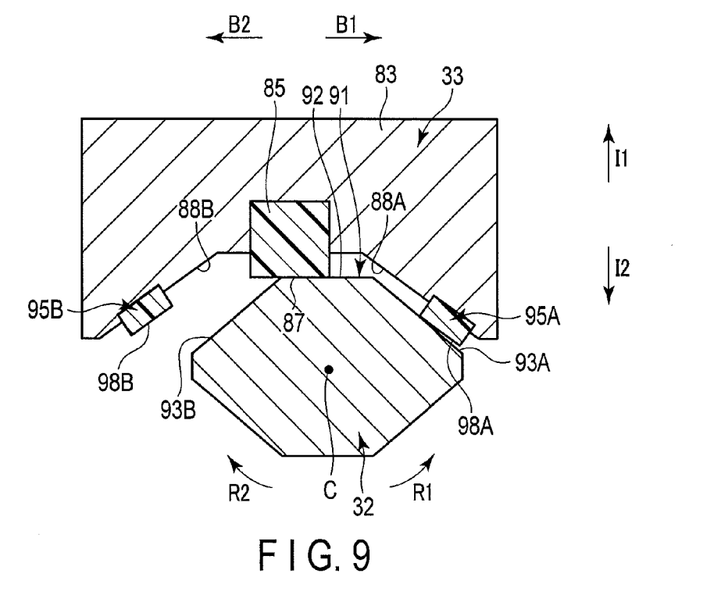
FIG. 9 is a cross-sectional view which schematically illustrates a state in which the distal treatment section according to the first embodiment has moved relative to the jaw in a first width direction from the state shown in FIG. 7.

FIG. 9 is a view illustrating a state in which the distal treatment section 32 has moved relative to the jaw 3 in the first width direction from the state (state in FIG. 7) in which the jaw 33 abuts on the receiving surface 92 of the distal treatment section 32. FIG. 9 illustrates the jaw 33 and distal treatment section 32 in a cross section perpendicular to the center axis C.

As illustrated in FIG. 9, when the distal treatment section 32 has moved toward the first width direction (direction of arrow B1 of FIG. 9) from the state (state of FIG. 7) in which the jaw 33 abuts on the receiving surface 92 of the distal treatment section 32, the inclined surface 93A of the distal treatment section 32 abuts on the insulation facing-surface 98A of the jaw insulation portion 95A. The dimension D2 of the spacing distance from the distal treatment section 32 at the insulation minimum spacing position P3 of the insulation facing-surface 98A becomes less than the dimension D1 of the spacing distance from the distal treatment section 32 at the electrode minimum spacing position P1 of the electrode facing-surface 88A. Thus, the dimension T2 of the width-directional spacing dimension from the distal treatment section 32 at the insulation minimum width-directional spacing position Q3 of the insulation facing-surface 98A becomes less than the dimension T1 of the width-directional spacing dimension from the distal treatment section 32 at the electrode minimum width-directional spacing position Q1 of the electrode facing-surface 88A. Thereby, in the state in which the abutment portion 87 abuts on the distal treatment section 32, at least a part of the insulation facing-surface 98A has a less width-directional spacing dimension from the distal treatment section 32 than any positions of the electrode facing-surface 88A. Therefore, in the state in which the distal treatment section 32 abuts on the insulation opposed-surface 98A of the jaw insulation portion 95A by the movement of the distal treatment section 32 relative to the jaw 33 in the first width direction, the electrode facing-surface 88A of the jaw electrode portion 83 is spaced apart, at any positions, from the distal treatment section 32.

On the other hand, when the distal treatment section 32 has moved relative to the jaw 33 in the second width direction from the state (state of FIG. 7) in which the jaw 33 abuts on the receiving surface 92 of the distal treatment section 32, the inclined surface 93B of the distal treatment section 32 abuts on the insulation facing-surface 98B of the jaw insulation portion 95B. In addition, in the state in which the distal treatment section 32 abuts on the insulation facing-surface 98B of the jaw insulation portion 95B by the movement of the distal treatment section 32 relative to the jaw 33 in the second width direction, the electrode facing-surface 88B of the jaw electrode section 83 is spaced apart, at any positions, from the distal treatment section 32.

As has been described above, in the treatment of the treatment target grasped between the jaw 33 and distal treatment section 32, even when the distal treatment section 32 has moved in the first width direction and second width direction by the pushing force from the jaw 33, the distal treatment section 32 abuts on the insulation facing-surface 98A of the jaw insulation portion 95A or the insulation facing-surface 98B of the jaw insulation portion 95B. Thereby, even when the distal treatment section 32 has moved in the first width direction and second width direction, it is possible to prevent the distal treatment section 32, which functions as the probe-side electrode portion and which performs the longitudinal vibration, from coming in contact with the jaw electrode portion 83. Thereby, the occurrence of a spark due to the contact of the distal treatment section 32 with the jaw electrode portion 83 can effectively be prevented, and the occurrence of a crack in the distal treatment section 32 can effectively be prevented.

Furthermore, as described above, since the bend extension portion 76 of the distal treatment section 32 bends in the first width direction, relative to the longitudinal axis L, the center of gravity of the distal treatment section 32 is positioned on the first width direction side with respect to the longitudinal axis L. Thus, by the pushing force acting from the jaw 33, the distal treatment section 32 tends to easily twist in such a state that a part on the first width direction side with respect to the center axis C moves toward the jaw 33. In other words, by the pushing force acting from the jaw 33, the distal treatment section 32 tends to easily twist in the first twist direction. In the present embodiment, the jaw insulation portion 95A is located on the first width direction side with respect to the center axis C. Thus, even when the distal treatment section 32 has twisted toward the first twist direction, the distal treatment section 32 exactly abuts on the insulation facing-surface 98A of the jaw insulation portion 95A. Therefore, it is possible to more exactly prevent the distal treatment section 32, which serves as the probe electrode portion, from coming in contact with the jaw electrode portion 83.

Second Embodiment

Next, a second embodiment of the present invention is described with reference to FIG. 10. In the second embodiment, the first embodiment is altered as follows. Incidentally, the same parts as in the first embodiment are denoted by like reference numerals, and a description thereof is omitted.

Figure 10:
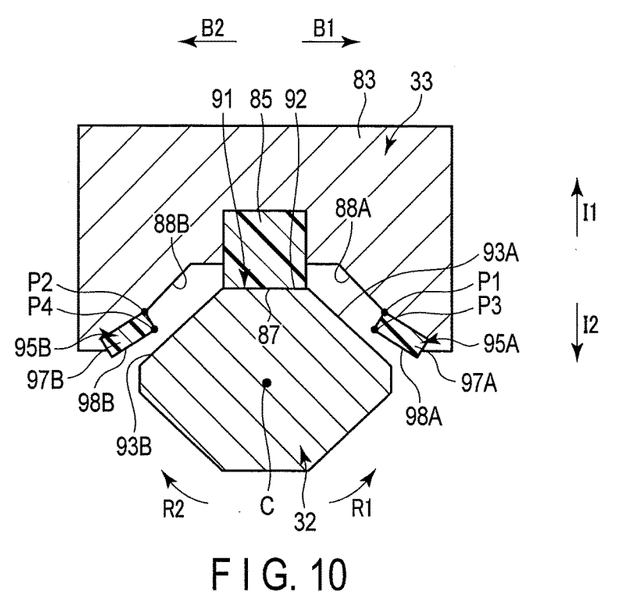
FIG. 10 is a cross-sectional view which schematically illustrates, in a cross section perpendicular to a center axis, a jaw and a distal treatment section according to a second embodiment.

FIG. 10 illustrates a distal treatment section 32 and a jaw 33 of this embodiment in a cross section perpendicular to the center axis C. As illustrated in FIG. 10, in the present embodiment, like the first embodiment, the jaw 33 is provided with an abutment portion 87, a jaw electrode portion 83 and jaw insulation portions 95A and 95B. Also in this embodiment, in each electrode facing-surface 88A or 88B of the jaw electrode unit 83, the spacing distance from the distal treatment section 32 in the state in which the abutment portion 87 abuts on the distal treatment section 32 varies in accordance with positions therein. In this embodiment, an insulation projection portion 97A projects toward the distal treatment section 32 from an electrode minimum spacing position P1 where the spacing distance from the distal treatment section 32 becomes minimum on the electrode facing-surface 88A. In addition, an insulation projection portion 97B projects toward the distal treatment section 32 from an electrode minimum spacing position P2 where the spacing distance from the distal treatment section 32 becomes minimum on the electrode facing-surface 88B. By adopting this configuration, in the present embodiment, like the first embodiment, in the state in which the abutment portion 87 abuts on the distal treatment section 32, at least a part of each insulation facing-surface 98A or 98B has a less spacing distance from the distal treatment section 32 than any positions of the electrode facing-surfaces 88A, 88B.

When the distal treatment section 32 has twisted about the center axis C in the first twist direction (direction of arrow R1 in FIG. 10) from the state in which the abutment portion 87 of jaw 33 abuts on the distal treatment section 32, the distal treatment section 32, which is the probe electrode portion, would easily come in contact with the electrode minimum spacing position P1 on the electrode opposed-surface 88A. In this embodiment, the insulation projection portion 97A projects toward the distal treatment section 32 from the electrode minimum spacing position P1 of the electrode facing-surface 88A. Thus, even when the distal treatment section 32 has twisted in the first twist direction, the distal treatment section 32 does not come in contact with the electrode minimum spacing position P1 of the electrode facing-surface 88A, and surely comes in contact with the insulation facing-surface 98A of the jaw insulation portion 95A.

In addition, when the distal treatment section 32 has twisted about the center axis C in the second twist direction (direction of arrow R2 in FIG. 10) from the state in which the abutment portion 87 of jaw 33 abuts on the distal treatment section 32, the distal treatment section 32, which is the probe electrode portion, would easily come in contact with the electrode minimum spacing position P2 on the electrode facing-surface 88B. In this embodiment, the insulation projection portion 97B projects toward the distal treatment section 32 from the electrode minimum spacing position P2 of the electrode opposed-surface 88B. Thus, even when the distal treatment section 32 has twisted in the second twist direction, the distal treatment section 32 does not come in contact with the electrode minimum spacing position P2 of the electrode facing-surface 88B, and surely comes in contact with the insulation facing-surface 98B of the jaw insulation portion 95B.

As described above, in the present embodiment, when the distal treatment section 32 has twisted in the first twist direction or the second twist direction, it is possible to more surely prevent the distal treatment section 32, which serves as the probe electrode portion, from coming in contact with the jaw electrode portion 83.

Third Embodiment

Next, a third embodiment of the present invention is described with reference to FIG. 11. In the third embodiment, the first embodiment is altered as follows. Incidentally, the same parts as in the first embodiment are denoted by like reference numerals, and a description thereof is omitted.

Figure 11:
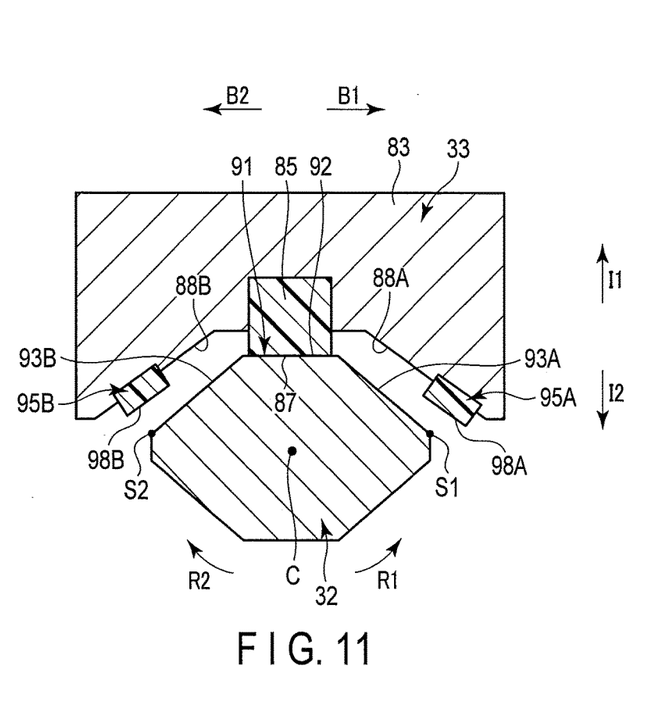
FIG. 11 is a cross-sectional view which schematically illustrates, in a cross section perpendicular to a center axis, a jaw and a distal treatment section according to a third embodiment.

FIG. 11 illustrates a distal treatment section 32 and a jaw 33 of this embodiment in a cross section perpendicular to the center axis C. As illustrated in FIG. 11, in the present embodiment, like the first embodiment, the jaw 33 is provided with an abutment portion 87, a jaw electrode portion 83 and jaw insulation portions 95A and 95B. Also in this embodiment, the distal treatment section 32 includes a treatment section facing-surface 91 which faces to the jaw 33. The treatment section opposed-surface 91 includes a receiving surface 92 and inclined surfaces 93A and 93B.

Here, a position on the treatment section facing-surface 91, where the distance from the center axis C becomes maximum, is referred to as a greatest abaxial distance position (S1 or S2). In this embodiment, the greatest abaxial distance position S1 is located at a first width direction side (direction side of arrow B1 in FIG. 11) end of the inclined surface 93A, and the greatest abaxial distance position S2 is located at a second width direction side (direction side of arrow B2 in FIG. 11) end of the inclined surface 93B. The jaw insulation portion 95A is disposed in the state in which the insulation facing-surface 98A faces to the greatest abaxial distance position S1. In addition, the jaw insulation portion 95B is disposed in the state in which the insulation facing-surface 98B faces to the greatest abaxial distance position S2. In other words, the insulation opposed-surface 98A of the jaw insulation portion 95A is provided at a position facing the greatest abaxial distance position S1 of the treatment section opposed-surface 91, and the insulation opposed-surface 98B of the jaw insulation portion 95B is provided at a position facing the greatest abaxial distance position S2 of the treatment section opposed-surface 91. In the present embodiment, like the first embodiment, in the state in which the abutment portion 87 abuts on the distal treatment section 32, at least a part of each insulation facing-surface 98A or 98B has a less spacing distance from the distal treatment section 32 than any positions of the electrode facing-surface 88A, 88B.

When the distal treatment section 32 has twisted about the center axis C in the first twist direction from the state in which the abutment portion 87 of jaw 33 abuts on the distal treatment section 32, the greatest abaxial distance position S1 of the treatment section facing-surface 91 would easily come in contact with the electrode facing-surface 88A. In this embodiment, the insulation facing-surface 98A of the jaw insulation portion 95A is opposed to the greatest abaxial distance position S1 of the treatment section facing-surface 91. Thus, even when the distal treatment section 32 has twisted in the first twist direction, the greatest abaxial distance position S1 of the distal treatment section 32 does not come in contact with the electrode facing-surface 88A, and surely comes in contact with the insulation facing-surface 98A of the jaw insulation portion 95A.

In addition, when the distal treatment section 32 has twisted about the center axis C in the second twist direction from the state in which the abutment portion 87 of jaw 33 abuts on the distal treatment section 32, the greatest abaxial distance position S2 of the treatment section facing-surface 91 would easily come in contact with the electrode facing-surface 88B. In this embodiment, the insulation facing-surface 98B of the jaw insulation portion 95B is opposed to the greatest abaxial distance position S2 of the treatment section facing-surface 91. Thus, even when the distal treatment section 32 has twisted in the second twist direction, the greatest abaxial distance position S2 of the distal treatment section 32 does not come in contact with the electrode facing-surface 88B, and surely comes in contact with the insulation facing-surface 98B of the jaw insulation portion 95B.

As described above, in the present embodiment, when the distal treatment section 32 has twisted in the first twist direction or the second twist direction, it is possible to more surely prevent the distal treatment section 32, which serves as the probe electrode portion, from coming in contact with the jaw electrode portion 83.

(Modifications)

Figure 12:
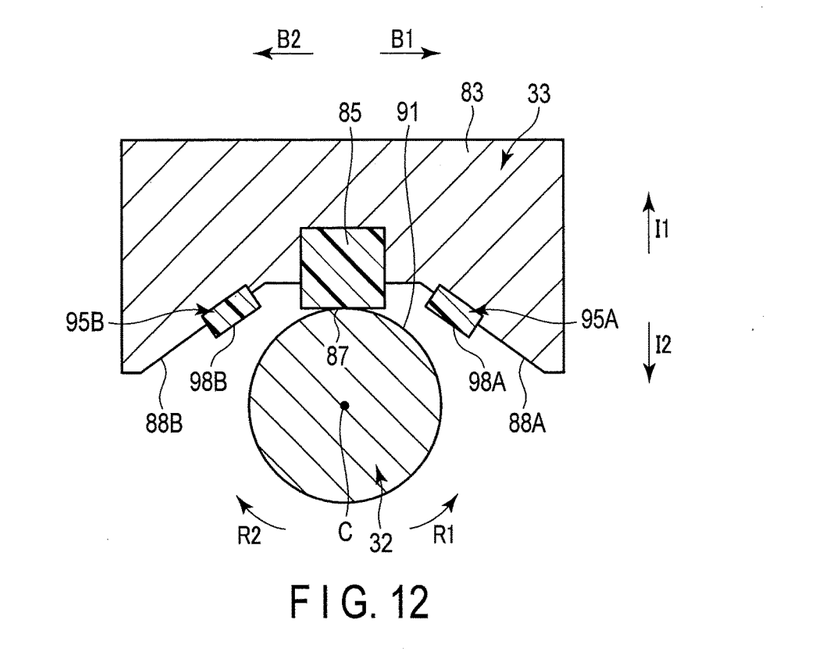
FIG. 12 is a cross-sectional view which schematically illustrates, in a cross section perpendicular to a center axis, a jaw and a distal treatment section according to a first modification.
Figure 13:
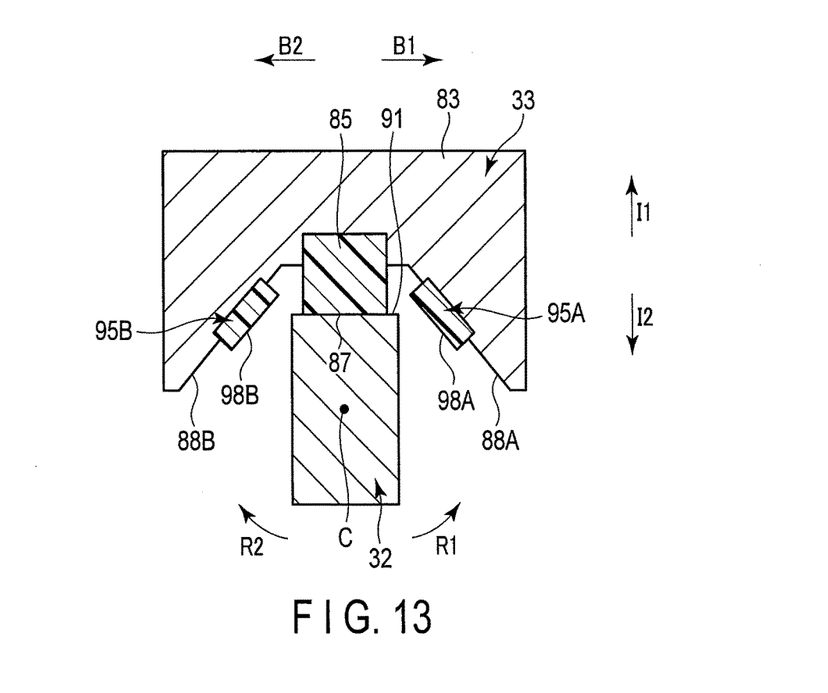
FIG. 13 is a cross-sectional view which schematically illustrates, in a cross section perpendicular to a center axis, a jaw and a distal treatment section according to a second modification.

In the above-described embodiments, the cross section of the distal treatment section 32, which is perpendicular to the center axis C, is formed in a substantially octagonal shape, but the embodiments are not restricted to this. For example, as illustrated in FIG. 12 as a first modification, the cross section of the distal treatment section 32, which is perpendicular to the center axis C, may be formed in a substantially circular shape. Besides, as illustrated in FIG. 13 as a second modification, the cross section of the distal treatment section 32, which is perpendicular to the center axis C, may be formed in a substantially rectangular shape. Also in the modifications illustrated in FIG. 12 and FIG. 13, the jaw 33 is provided with an abutment portion 87, a jaw electrode portion 83 and jaw insulation portions 95A and 95B. In the state in which the abutment portion 87 abuts on the distal treatment section 32, at least a part of each insulation facing-surface 98A or 98B has a less spacing distance from the distal treatment section 32 than any positions of the electrode facing-surface 88A, 88B.

By adopting this configuration, even when the distal treatment section 32 has twisted about the center axis C, the distal treatment section 32 abuts on the insulation facing-surface 98A of the jaw insulation portion 95A or the insulation facing-surface 98B of the jaw insulation portion 95B. Thereby, even when the distal treatment section 32 has twisted, it is possible to prevent the distal treatment section 32, which functions as the probe-side electrode unit and which performs the longitudinal vibration, from coming in contact with the jaw electrode portion 83. Furthermore, by adopting this configuration, even when the distal treatment section 32 has moved in the first width direction and second width direction, the distal treatment section 32 abuts on the insulation facing-surface 98A of the jaw insulation portion 95A or the insulation facing-surface 98B of the jaw insulation portion 95B. Thereby, even when the distal treatment section 32 has moved in the first width direction and second width direction, it is possible to prevent the distal treatment section 32, which functions as the probe-side electrode portion and which performs the longitudinal vibration, from coming in contact with the jaw electrode portion 83.

From the above-described embodiments and modifications, the jaw (33) of the grasping treatment apparatus (1) includes the abutment portion (87) which is formed of an insulative material and can abut on the distal treatment section (32) in the state in which the jaw (33) is closed relative to the distal treatment section (32); and the jaw electrode portion (83) which is formed of an electrically conductive material in a different part from the abutment portion (87) and does not come in contact with the distal treatment section (32) in the state in which the abutment portion (87) abuts on the distal treatment section (32). In addition, the jaw electrode portion (83) includes the electrode facing-surfaces (88A, 88B) which are spaced apart from the distal treatment section (32) and face to the distal treatment section (32) in the state in which the abutment portion (87) abuts on the distal treatment section (32). Besides, the jaw (33) of the grasping treatment apparatus (1) includes the jaw insulation portions (95A, 95B) each of which is formed of an insulative material at position spaced apart from the abutment portion (87) in the first width direction (B1) and second width direction (B2). Each jaw insulation portion (95A or 95B) includes the insulation facing-surface (98A or 98B) which is spaced apart from the distal treatment section (32) and faces to the distal treatment section (32) in the state in which the abutment portion (87) abuts on the distal treatment section (32). In the state in which the abutment portion (87) abuts on the distal treatment section (32), at least a part of each insulation facing-surface (98A or 98B) has a less spacing distance from the distal treatment section (32) than any positions of the electrode facing-surfaces (88A, 88B).

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A grasping treatment apparatus, comprising:
a vibration transmission member having a distal portion; and
a jaw configured to open and close relative to the distal portion of the vibration transmission member, the jaw having:
an electrode portion;
an abutment portion that is narrower than the electrode portion in a width direction transverse to a center axis of the jaw and transverse to opening and closing directions of the jaw, the abutment portion being configured to contact the distal portion so as to prevent contact between the electrode portion and the distal portion when the jaw is in a closed position;
an insulation portion spaced apart from the abutment portion in the width direction; and
an electrode exposed portion of the electrode portion disposed at least between the abutment portion and the insulation portion in the width direction, each of the abutment portion and the insulation portion protruding from the electrode exposed portion toward the distal portion of the vibration transmission member, a protruding amount of the insulation portion from the electrode exposed portion being smaller than a protruding amount of the abutment portion from the electrode exposed portion, the insulation portion being fixed to a continuous surface of the electrode exposed portion.

2. The grasping treatment apparatus of claim 1, wherein the distal portion has a curved portion in which a center axis of the vibration transmission member is curved in the width direction.

3. The grasping treatment apparatus of claim 1, wherein the insulation portion is apart from the distal portion in a neutral state in which the jaw in the closed position is parallel to the distal portion and does not deviate from the distal portion in the width direction.

4. The grasping treatment apparatus of claim 3, wherein a first distance between the distal portion and the electrode portion is more than a second distance between the distal portion and the insulation portion in the neutral state.

5. The grasping treatment apparatus of claim 4, wherein the distal portion abuts the insulation portion when the distal portion twists about a center axis of the vibration transmission member from the neutral state or moves relative to the jaw in the width direction from the neutral state.

6. A grasping treatment apparatus for cooperating with a vibration transmission member having a distal portion, comprising:
a jaw configured to open and close relative to the distal portion of the vibration transmission member, the jaw having:
an electrode portion;
an abutment portion that is narrower than the electrode portion in a width direction transverse to a center axis of the jaw and transverse to opening and closing directions of the jaw, the abutment portion being configured to contact the distal portion so as to prevent contact between the electrode portion and the distal portion when the jaw is in a closed position;
an insulation portion spaced apart from the abutment portion in the width direction; and
an electrode exposed portion of the electrode portion disposed at least between the abutment portion and the insulation portion in the width direction, each of the abutment portion and the insulation portion protruding from the electrode exposed portion toward the distal portion of the vibration transmission member, a protruding amount of the insulation portion from the electrode exposed portion being smaller than a protruding amount of the abutment portion from the electrode exposed portion, the insulation portion being fixed to a continuous surface of the electrode exposed portion.

* * * * *